(12) United States Patent
Tamura et al.

(10) Patent No.: US 9,046,484 B2
(45) Date of Patent: Jun. 2, 2015

(54) PLASMON SENSOR

(71) Applicant: PANASONIC CORPORATION, Osaka (JP)

(72) Inventors: Masaya Tamura, Osaka (JP); Hiroshi Kagata, Osaka (JP); Kiyoshi Hashimotodani, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 13/776,043

(22) Filed: Feb. 25, 2013

(65) Prior Publication Data

US 2013/0163001 A1    Jun. 27, 2013

Related U.S. Application Data

(63) Continuation of application No. PCT/JP2011/005448, filed on Sep. 28, 2011.

(30) Foreign Application Priority Data

Oct. 7, 2010  (JP) .................................. 2010-227094

(51) Int. Cl.
*G01N 21/552*    (2014.01)
*G02B 5/00*    (2006.01)
*G01N 33/569*    (2006.01)

(52) U.S. Cl.
CPC .............. *G01N 21/553* (2013.01); *G02B 5/008* (2013.01); *G01N 33/56983* (2013.01)

(58) Field of Classification Search
None
See application file for complete search history.

(56) References Cited

U.S. PATENT DOCUMENTS

| 6,090,545 | A  | * | 7/2000 | Wohlstadter et al. | ......... | 435/6.11 |
| 6,096,550 | A  | * | 8/2000 | Argo | ................................. | 436/5 |
| 6,331,276 | B1 | * | 12/2001 | Takei et al. | ................ | 422/82.09 |
| 2004/0016642 | A1 | | 1/2004 | Miyazaki et al. | | |

(Continued)

FOREIGN PATENT DOCUMENTS

| CN | 1339105 A | 3/2002 |
| CN | 101131387 A | 2/2008 |

(Continued)

OTHER PUBLICATIONS

Afanas'ev, B.N., et al., "A Correlation between the Hydrophilicity of a Metal and Its Surface Tension. Calculation of the Bond Energy of Water Molecules Adsorbed on an Uncharged Metal Surface," Protection of Metals, vol. 36, No. 1, 2000, pp. 25-30. Translated from Zashchita Metallov, vol. 36, No. 1, 2000, pp. 29-34.*

(Continued)

*Primary Examiner* — Gordon J Stock, Jr.
(74) *Attorney, Agent, or Firm* — McDermott Will & Emery LLP

(57) ABSTRACT

A plasmon sensor includes a supporter, a first metal layer on a lower surface of the first supporter, and a second metal layer having an upper surface facing a lower surface of the first metal layer. A hollow space is provided between the first and second metal layers, and is configured to be filled with a test sample containing a medium. The area of the first metal layer is smaller than the area of the upper surface of the supporter. The supporter has a region having hydrophilic property and facing and contacting the hollow space. This the plasmon sensor has a small size and a simple structure.

27 Claims, 14 Drawing Sheets

(56) References Cited

U.S. PATENT DOCUMENTS

| | | |
|---|---|---|
| 2007/0048796 A1 | 3/2007 | Kubo et al. |
| 2008/0020409 A1* | 1/2008 | Pawlak et al. ............... 435/7.23 |
| 2009/0051901 A1* | 2/2009 | Shen et al. .................... 356/73 |
| 2009/0109422 A1* | 4/2009 | Handa et al. .................. 356/39 |
| 2010/0097611 A1* | 4/2010 | Song ............................. 356/445 |

FOREIGN PATENT DOCUMENTS

| | | |
|---|---|---|
| JP | 2005-181296 A | 7/2005 |
| JP | 2005-300460 A | 10/2005 |
| JP | 2007-057504 A | 3/2007 |

OTHER PUBLICATIONS

Zynio et al., "Bimetallic Layers Increase Sensitivity of Affinity Sensors Based on Surface Plasmon Resonance," Sensors 2002, vol. 2, ISSN 1424-8220 by MDPI, pp. 62-70.

J. Homola, et al. "Surface Plasmon Resonance Sensors: Review," Sensors and Actuators B, vol. 54 (1999), Elsevier, pp. 3-15.

* cited by examiner

US 9,046,484 B2

PLASMON SENSOR

This is a continuation of PCT International Application No. PCT/JP2011/005448 filed on Sep. 28, 2011 which claims a priority to Japanese Patent Application No. 2010-227094 filed on Oct. 7, 2010.

TECHNICAL FIELD

The present invention relates to a plasmon sensor utilizing a surface plasmon resonance and being adaptable for detecting, e.g. viruses.

BACKGROUND ART

FIG. 14 is a sectional view of conventional plasmon sensor 100 adapted for detecting viruses, for example. Plasmon sensor 100 includes prism 101, metal layer 102 having a smooth surface situated on a lower surface of prism 101, insulation layer 103 having a predetermined dielectric constant and having a smooth surface situated on a lower surface of metal layer 102, and acceptors 104 fixed to a lower surface of insulation layer 103.

A surface plasmon wave that is a compression wave of electrons exists at the interface between metal layer 102 and insulation layer 103. Light source 105 located above prism 101 applies p-polarized light to prism 101 under a condition of total reflection. At this moment, an evanescent wave is generated on surfaces of metal layer 102 and insulation layer 103. The light totally reflected on the surface of metal layer 102 enters into detector 106 that detects an intensity of the light.

Here, energy of the light supplied from light source 105 is used to excite the surface plasmon wave when a matching condition of wave numbers under which the wave number of the evanescent wave is consistent with the wave number of the surface plasmon wave is fulfilled, thereby decreasing the intensity of the reflected light. The matching condition of wave numbers is dependent upon an incidence angle of the light irradiated from light source 105. Therefore, the intensity of the reflected light decreases at a certain incidence angle when measured with detector 106 while changing the incidence angle.

A resonance angle at which the intensity of the reflected light becomes the minimum depends on a dielectric constant of insulation layer 103. The dielectric constant of insulation layer 103 changes when an analyte which is an object substance in a test sample is bound specifically with acceptors 104 and form a product of specific binding on the lower surface of insulation layer 103, which in turn changes the resonance angle. This allows a binding strength, speed and the like of the specific binding reaction between the analyte and acceptors 104 to be detected by monitoring the change in the resonance angle.

Plasmon sensor 100 includes light source 105 for supplying the p-polarized light and prism 101 disposed on metal layer 102, thus having a large size and a complex structure.

Patent Literature 1 discloses a conventional plasmon sensor similar to plasmon sensor 100.

CITATION LIST

Patent Literature 1: Japanese Patent Laid-Open Publication No. 2005-181296

SUMMARY OF THE INVENTION

A plasmon sensor includes a supporter, a first metal layer on a lower surface of the first supporter, and a second metal layer having an upper surface facing a lower surface of the first metal layer. A hollow space is provided between the first and second metal layers, and is configured to be filled with a test sample containing a medium. The area of the first metal layer is smaller than the area of the upper surface of the supporter. The supporter has a region having hydrophilic property and facing and contacting the hollow space.

This plasmon sensor has a small size and a simple structure.

DETAIL DESCRIPTION OF PREFERRED EMBODIMENTS

Exemplary Embodiment 1

Figure 1:
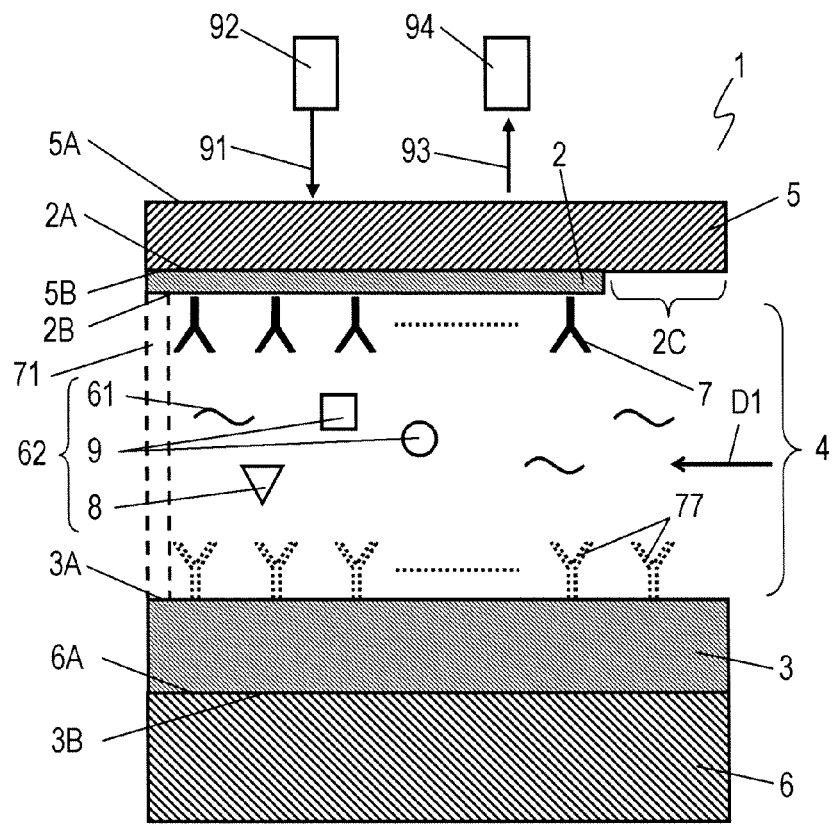
FIG. 1 is a cross-sectional view of a plasmon sensor according to Exemplary Embodiment 1 of the present invention.

FIG. 1 is a cross-sectional view of plasmon sensor 1 according to Exemplary Embodiment 1 of the present invention. Plasmon sensor 1 includes metal layer 2 and metal layer 3 disposed below metal layer 2 facing metal layer 2 across hollow space 4. Metal layers 2 and 3 are made of metal, such as gold or silver. Hollow space 4 is configured to be filled with test sample 62 of a liquid form when plasmon sensor 1 is used, and is sandwiched substantially between metal layers 2 and 3. Test sample 62 contains target analyte 8, non-specific analyte 9, and medium 61. Medium 61 contains hydrophilic fluid, such as a hydrophilic liquid or a hydrophilic gel, and carries target analyte 8 and non-specific analyte 9.

Metal layer 2 cannot maintain its shape by itself since it generally has a thickness not larger than 100 nm. Upper surface 2A of metal layer 2 is therefore fixed onto lower surface 5B of supporter 5 to maintain the shape of metal layer 2. Metal layer 3 is fixed to and held on upper surface 6A of supporter 6.

Electromagnetic wave 91 enters onto upper surface 2A of metal layer 2. Metal layer 2, being made of gold, preferably has a thickness ranging from 35 nm to 45 nm in the case that electromagnetic wave 91 is visible light. Any thickness outside of this range decreases the amount of reflective absorption of electromagnetic wave 91 by the surface plasmon resonance.

Metal layer 3, being made of gold, preferably has a thickness not smaller than 100 nm. If the thickness is less than 100 nm, incident electromagnetic wave 91 (i.e., visible light) penetrates metal layer 3, which decreases the amount of reflective absorption of electromagnetic wave 91 by the surface plasmon resonance. As stated, metal layer 2 is thinner than metal layer 3.

Plasmon sensor 1 may include spacer 71, such as a post or a wall, which retains metal layers 2 and 3 in order to maintain a predetermined distance between metal layers 2 and 3. This structure provides hollow space 4 in plasmon sensor 1.

Electromagnetic wave source 92 is placed above upper surface 2A of metal layer 2, that is, at one side of metal layer 2 opposite to metal layer 3. Electromagnetic wave source 92 applies electromagnetic wave 91 onto metal layer 2 from above upper surface 2A. According to Embodiment 1, electromagnetic wave source 92 radiates electromagnetic wave 91 toward upper surface 5A of supporter 5, and applies electromagnetic wave 91 to metal layer 2 from above upper surface 2A through supporter 5.

Figure 14:
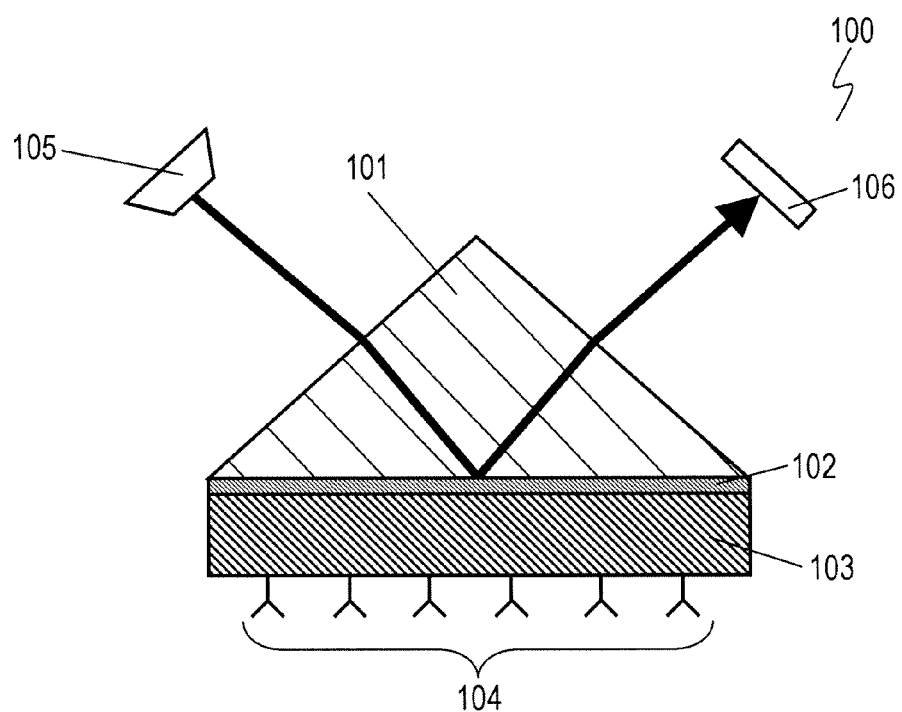
FIG. 14 is a cross-sectional view of a conventional plasmon sensor.

An operation of plasmon sensor 1 will be described below. According to Embodiment 1, electromagnetic wave 91 is light, and electromagnetic wave source 92 is a light source. Electromagnetic wave source 92, or the light source, does not include any such device as a polarizing plate for aligning polarization of the light. Unlike conventional plasmon sensor 100 shown in FIG. 14, plasmon sensor 1 can excite surface plasmon resonance not only by p-polarized light but also by s-polarized light.

Electromagnetic wave 91 applied to upper surface 2A from above metal layer 2 is supplied to hollow space 4 by passing through metal layer 2, and reaches upper surface 3A of metal layer 3. Electromagnetic wave 91 generates surface plasmon on lower surface 2B of metal layer 2 at the side facing hollow space 4, and also on upper surface 3A of metal layer 3 at the side facing hollow space 4. Surface plasmon resonance is excited on lower surface 2B of metal layer 2 when a wave number of electromagnetic wave 91 supplied to hollow space 4 matches with a wave number of the surface plasmon generated on lower surface 2B of metal layer 2. Surface plasmon resonance is also excited on upper surface 3A of metal layer 3 when the wave number of electromagnetic wave 91 matches with that of the surface plasmon generated on upper surface 3A of metal layer 3.

The frequency for generating the surface plasmon resonance can be controlled by adjusting at least one of structural factors, such as a shape, mainly a thickness, of metal layer 2, a shape, mainly a thickness, of metal layer 3, a spatial distance between metal layers 2 and 3, a dielectric constant of metal layer 2, a dielectric constant of metal layer 3, a dielectric constant of medium 61 between metal layers 2 and 3, and distribution of the dielectric constant of medium 61.

Detector 94 is placed above upper surface 2A of metal layer 2 for detecting electromagnetic wave 93 such as light. Detector 94 receives electromagnetic wave 93, such as the light, reflected or radiated from plasmon sensor 1 when plasmon sensor 1 receives electromagnetic wave 91 supplied from electromagnetic wave source 92.

According to Embodiment 1, the thickness of metal layer 2 is smaller than about 100 nm. If metal layer 2 is thicker than 100 nm, surface plasmon resonance cannot be excited on any of lower surface 2B of metal layer 2 and upper surface 3A of metal layer 3 since metal layer 2 prevents penetration of a certain wavelength component of the electromagnetic wave (i.e., light) that causes the surface plasmon resonance.

Metal layer 2 having the thickness not larger than about 100 nm cannot maintain its shape by itself. Supporter 5 is fixed onto upper surface 2A of metal layer 2 in order to maintain the shape of metal layer 2. Supporter 5 is made of material hardly attenuating electromagnetic wave 91 since supporter 5 needs to transmit electromagnetic wave 91 efficiently to metal layer 2. According to Embodiment 1, supporter 5 is made of optically transparent material, such as glass or transparent plastic that allows light to pass through the material efficiently since electromagnetic wave 91 is light. Supporter 5 preferably has a thickness as small as practically possible within a range tolerable from a view point of physical strength.

Metal layer 3 has a thickness not smaller than about 100 nm. Metal layer 3 having a thickness less than 100 nm may cause a part of the electromagnetic wave supplied to hollow space 4 through metal layer 2 to pass through metal layer 3 and leak to the outside of hollow space 4. This leaking decreases the sensitivity of plasmon sensor 1 when the energy of the electromagnetic wave is lost partially to the outside of hollow space 4 instead of being used for excitation of the surface plasmon resonance as intended. The sensitivity of plasmon sensor 1 can be thus increased by making metal layer 2 thinner than metal layer 3.

The above structure confines electromagnetic wave 91, light, supplied from electromagnetic wave source 92 inside hollow space 4 to excite the surface plasmon resonance. In addition to the surface plasmon resonance, this structure also excites surface plasmon polaritons due to coupling of electromagnetic wave 91 with the surface plasmon, which results in absorption of the supplied electromagnetic wave 91, thereby preventing only a component of absorbed frequency from being radiated while allowing the other frequency components to radiate as electromagnetic wave 93.

Lower surface 3B of metal layer 3 is fixed onto upper surface 6A of supporter 6 to retain the shape of metal layer 3.

Electromagnetic wave 91, such as light, supplied to plasmon sensor 1 is prevented preferably from passing through metal layer 3 in order to increase the sensitivity of plasmon sensor 1. For this reason, supporter 6 is made preferably of material that cuts off electromagnetic wave 91, such as light. For example, supporter 6 is made of a metal or a semiconductor having a thickness not smaller than 100 nm.

The thickness of supporter 6 is preferably larger than the thickness of supporter 5 so as to increase the physical strength of plasmon sensor 1 as well as to prevent a possible change in the sensing characteristic of plasmon sensor 1 due to deformation of its shape while being used.

In plasmon sensor 1, acceptors 7 are disposed on lower surface 2B of metal layer 2 at the side facing hollow space 4. Acceptors 77 similar to acceptors 7 may be provided on upper surface 3A of metal layer 3 at the side facing hollow space 4. Or, only acceptors 77 can be provided on upper surface 3A of metal layer 3 out of surfaces 2B and 3A of metal layers 2 and 3 of plasmon sensor 1 while acceptors 7 is not necessarily provided on lower surface 2B of metal layer 2 out of surfaces 2B and 3A.

Figure 2:
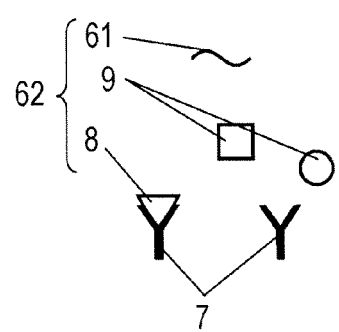
FIG. 2 is a schematic view of the plasmon sensor according to Embodiment 1 for illustrating a specific binding between an acceptor and an analyte.

Acceptor 7 is bound specifically with analyte 8 when test sample 62 containing target analyte 8 contacts acceptors 7. FIG. 2 is a schematic view illustrating the specific binding between acceptor 7 and target analyte 8. Test sample 62 contains non-specific analyte 9 and target analyte 8 as a specific analyte. Acceptors 7 is selectively bound specifically only with target analyte 8, but is not bound specifically with non-specific analyte 9.

Figure 3A:
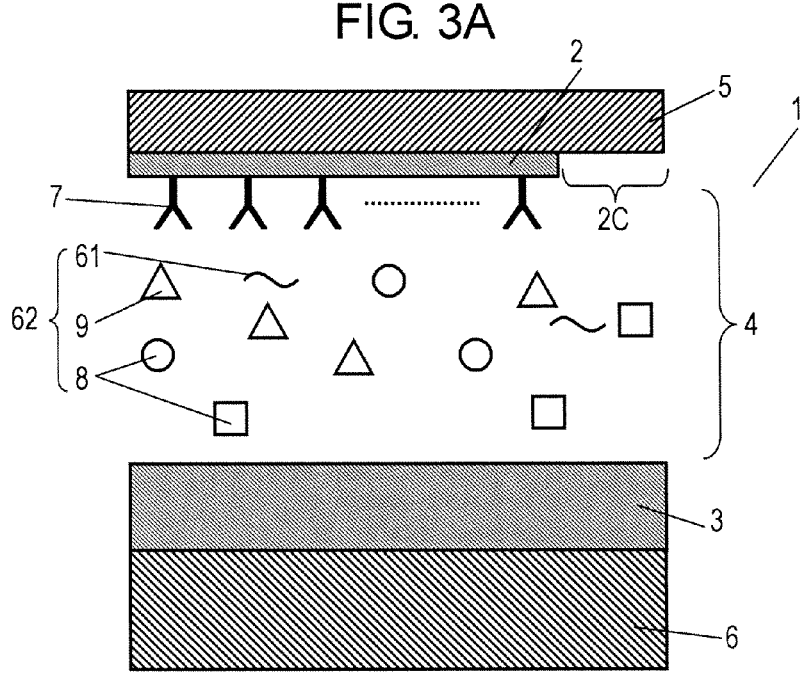
FIG. 3A is a cross-sectional view of the plasmon sensor according to Embodiment 1.
Figure 3B:
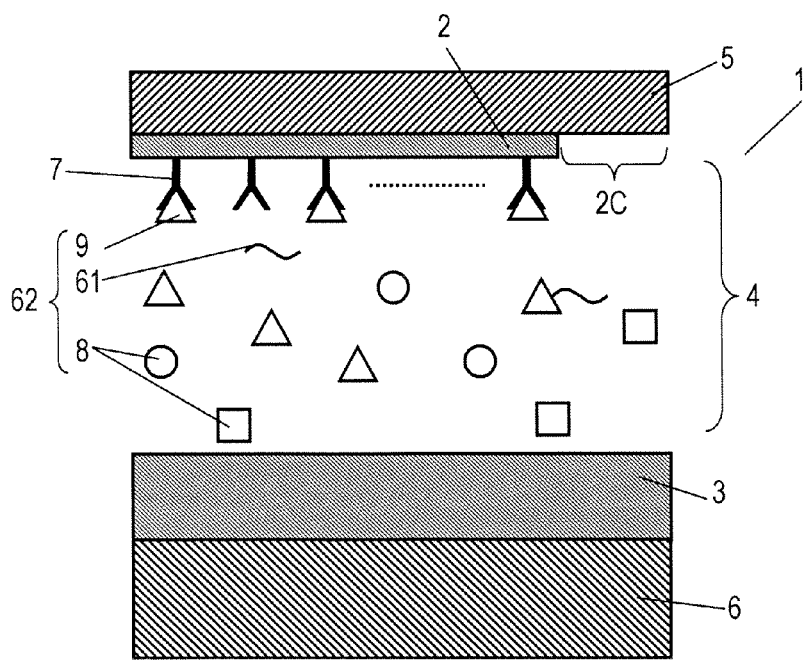
FIG. 3B is a cross-sectional view of the plasmon sensor according to Embodiment 1.

FIGS. 3A and 3B are cross-sectional views of plasmon sensor 1 for illustrating an operation of plasmon sensor 1. When test sample 62 containing non-specific analyte 9 and target analyte 8 is injected by capillary phenomenon into hollow space 4 which is in vacuum or is filled with air, as shown in FIG. 3A, the state of hollow space 4, particularly the dielectric constant of hollow space 4, changes. This accordingly changes a resonance frequency that is a frequency of the surface plasmon resonance generated in plasmon sensor 1.

Then, when acceptors 7 provided on lower surface 2B of metal layer 2 is bound specifically with analyte 8, as shown in FIG. 3B, a thickness of organic substance and a relative dielectric constant around lower surface 2B of metal layer 2 change, accordingly changing a dielectric constant of medium 61 as well as distribution of the dielectric constant between metal layers 2 and 3. Thus, the resonance frequency of plasmon sensor 1 changes with the progress of the specific binding between acceptors 7 and analyte 8. Hence, a state of the specific binding between acceptors 7 and analyte 8, particularly strength of the specific binding, a speed and the like of the binding can be detected by observing the change in the resonance frequency.

Figure 4A:
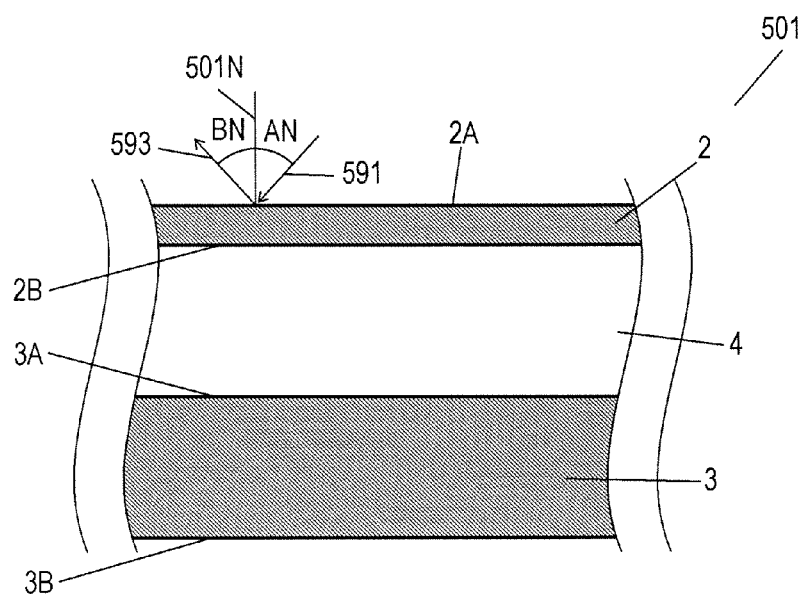
FIG. 4A is a schematic view of an analysis model of an electromagnetic field simulation of the plasmon sensor according to Embodiment 1.
Figure 4B:
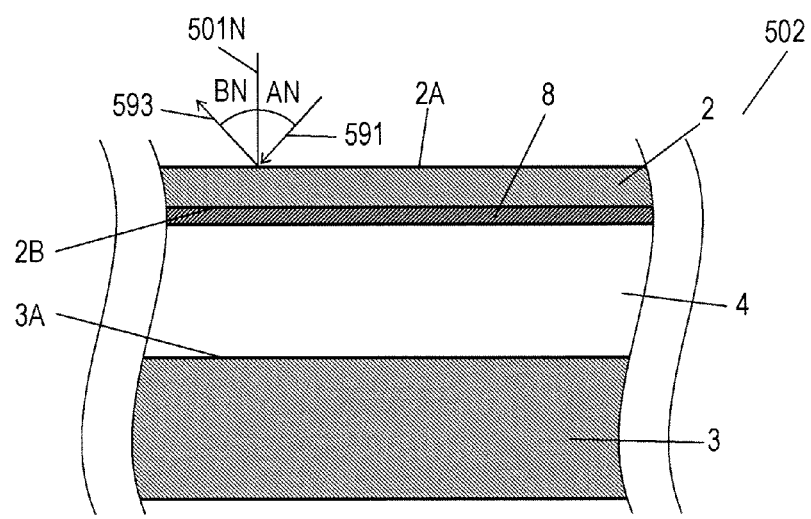
FIG. 4B is a schematic view of another analysis model of the electromagnetic field simulation of the plasmon sensor according to Embodiment 1.

The change in the frequency of the surface plasmon resonance that occurs in plasmon sensor 1 due to the specific binding between acceptors 7 and analyte 8 will be described below by referring to electromagnetic field simulations. FIGS. 4A and 4B are schematic views of analysis models 501 and 502 for the electromagnetic field simulations of plasmon sensor 1, respectively.

In analysis model 501 shown in FIG. 4A, metal layer 2 is made of silver, and has a thickness of 30 nm. Metal layer 3 is made of silver, and has a thickness of 130 nm. The distance between metal layers 2 and 3 is 160 nm, and hollow space 4 is filled with air having a relative dielectric constant of 1.0. Both spaces above upper surface 2A of metal layer 2 and below lower surface 3B of metal layer 3 are filled with air. In analysis model 501, metal layers 2 and 3 and hollow space 4 extend infinitely.

Analysis model 502 shown in FIG. 4B is identical to analysis model 501 shown in FIG. 4A except that analyte 8 is provided on lower surface 2B of metal layer 2. Analyte 8 has a thickness of 10 nm and a relative dielectric constant of 3.0. The distance between analyte 8 and upper surface 3A of metal layer 3 is 150 nm, and hollow space 4 is filled with air having a relative dielectric constant of 1.0. Both spaces above upper surface 2A of metal layer 2 and below lower surface 3B of metal layer 3 are filled with air. In analysis model 502, metal layers 2 and 3 and hollow space 4 extend infinitely.

A dielectric function of the silver to form metal layers 2 and 3 can be drawn by converting experimental data of refractive indices described in "Handbook of Optical Constants of Solids (Palik, Edward D. in 1998)". In analysis models 501 and 502 shown in FIGS. 4A and 4B, acceptors 7 are not modeled to simplify the simulation analyses.

The electromagnetic field simulation analyses were conducted on analysis models 501 and 502 by sending electromagnetic wave 591 at descending angle AN of 45 degrees with respect to normal direction 501N perpendicular to upper surface 2A of metal layer 2, and by detecting electromagnetic wave 593 radiated from upper surface 2A of metal layer 2 at an ascending angle of −45 degrees.

Figure 5:
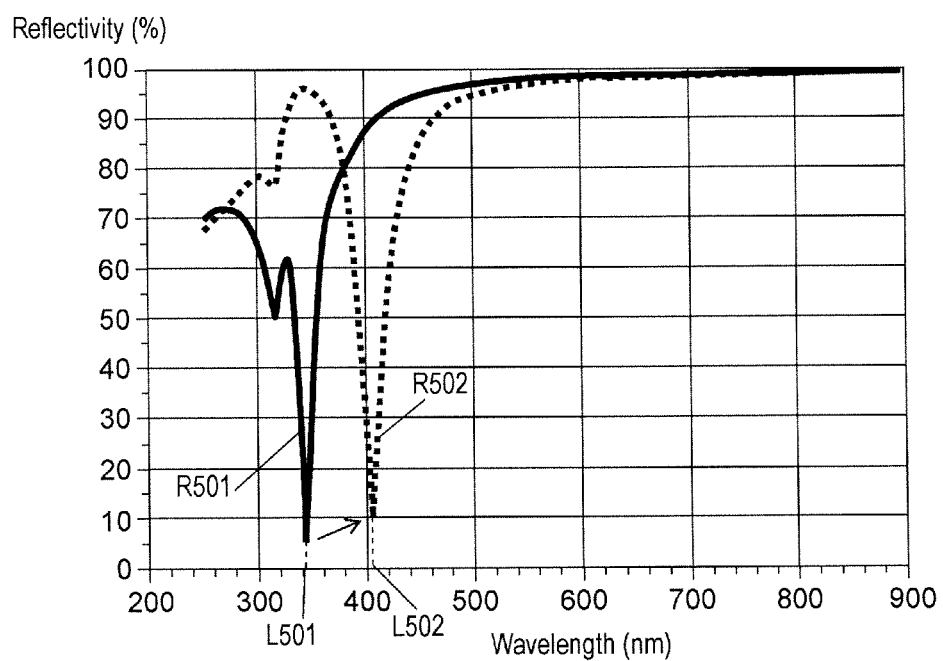
FIG. 5 shows an analysis result of the electromagnetic field simulation of the plasmon sensor according to Embodiment 1.

FIG. 5 shows a result of the electromagnetic field simulations. In FIG. 5, the horizontal axis represents the wavelength of electromagnetic wave 591, and the vertical axis represents a reflectivity which is the ratio of power of electromagnetic wave 593 to power of electromagnetic wave 591. FIG. 5 shows respective reflectivities R501 and R502 of analysis models 501 and 502.

As shown in FIG. 5, the value of reflectivity R501 decreases sharply and locally near the wavelength of 340 nm of electromagnetic wave 591. Around resonant wavelength L501 of the electromagnetic wave at which the reflectivity becomes the smallest, the wave number of the electromagnetic wave supplied to hollow space 4 matches with the wave number of the surface plasmon generated on lower surface 2B of metal layer 2, and the surface plasmon resonance is hence excited on lower surface 2B of metal layer 2. Similarly, the surface plasmon resonance is excited on upper surface 3A of metal layer 3 since the wave number of electromagnetic wave 591 supplied to hollow space 4 matches with the wave number of the surface plasmon generated on upper surface 3A of metal layer 3 around resonant wavelength L501.

In analysis model 502 shown in FIG. 4B, resonant wavelength L502 at which the value of reflectivity R502 sharply and locally decreases is longer than resonant wavelength L501 of analysis model 501 by about 70 nm, as shown in FIG. 5. The value of the relative dielectric constant of analyte 8 attached onto lower surface 2B of metal layer 2 of analysis model 502 shown in FIG. 4B changes to decrease the resonance frequency of generating the surface plasmon resonance excited on lower surface 2B of metal layer 2, thereby increasing in the resonant wavelength by about 70 nm.

Thus, the result of the simulation analyses shown in FIG. 5 indicates that the surface plasmon resonance is excited on lower surface 2B of metal layer 2. The change in the state of the medium around lower surface 2B of metal layer 2 can be detected by measuring the change in the resonance frequency (resonant wavelength).

Plasmon sensor 1 detects not only the change in the resonance frequency but also a change in the reflectivity. Plasmon sensor 1 can thus detect the change in the state of the medium around lower surface 2B of metal layer 2 by using these two detected indices simultaneously, hence having a high detecting performance. The state of the medium in hollow space 4 means a state that the material fills partially or entirely hollow space 4, such as composition of the material and distribution of the material within hollow space 4.

In plasmon sensor 1, medium 61 of test sample 62 containing analyte 8 is a liquid, and it is introduced into hollow space 4 by capillary phenomenon. However, it is difficult to introduce test sample 62 into hollow space 4 if lower surface 5B of supporter 5 is covered entirely with metal layer 2 and also upper surface 6A of supporter 6 is covered entirely with metal layer 3, for instance, since metal layers 2 and 3 have high hydrophobic properties. In plasmon sensor 1 according to Embodiment 1, metal layer 2 has a surface area smaller than the area of lower surface 5B of supporter 5. Supporter 5 has hydrophilic property. This structure provides region 2C of lower surface 5B of supporter where metal layer 2 does not exist on lower surface 5B of supporter 5, as shown in FIG. 1. As a result, test sample 62 can be introduced easily by the capillary phenomenon into region 2C since lower surface 5B of supporter 5 having the hydrophilic property is exposed and faces hollow space 4 in region 2C. As shown in FIG. 1, region 2C that exposes supporter 5 having the hydrophilic property exists in a part or all of lower surface 5B of supporter 5 from an edge of lower surface 5B of supporter 5. Test sample 62 can be introduced into hollow space 4 easily by the capillary phenomenon when test sample 62 is put into hollow space 4 in the direction D1 from region 2C toward lower surface 2B of metal layer 2 since test sample 62 contacts region 2C easily. However, test sample 62 can be introduced easily by the capillary phenomenon even if region 2C that exposes supporter 5 having the hydrophilic property does not exist in a part or all of lower surface 5B of supporter 5 from the edge of lower surface 5B of supporter 5, that is, region 2C provided in the center region of lower surface 5B of supporter 5, for instance, allows the test sample to be introduced more easily than the sensor which does not have region 2C. In addition, test sample 62 can be introduced easily into hollow space 4 by the capillary phenomenon even if test sample 62 is put into any direction other than the direction D1 because test sample 62 contacts region 2C. Supporter 6 does not necessarily have hydrophilic property.

According to Embodiment 1, "hollow space 4" is a space into which test sample 62 can be put, "lower surface 5B of supporter 5" is a surface contacting hollow space 4 and metal layer 2, and "upper surface 6A of supporter 6" is indicates a surface contacting hollow space 4 and metal layer 3.

According to Embodiment 1, the "supporter having hydrophilic property" means a supporter that has hydrophilicity in at least a region contacting the hollow space. Thus, the supporter may be made entirely of a hydrophilic material, or may be made mostly of a hydrophobic material (i.e., resin material) and at least a part of the region of the supporter that faces and contacts hollow space 4 is made of a hydrophilic material. Alternatively, the supporter may be made mainly of a hydrophobic resin, and a film of hydrophilic material is coated on at least a region of the resin-made supporter contacting hollow space 4.

Acceptors 7 are disposed on lower surface 2B of metal layer 2 in plasmon sensor 1 shown in FIG. 1. Acceptors 7 and 77 may not be provided on the surfaces of metal layers 2 and 3. Plasmon sensor 1 without acceptors 7 (77) disposed on any of lower surface 2B of metal layer 2 and upper surface 3A of metal layer 3, that is, plasmon sensor 1 not provided with acceptors 7 (77), can still detect a type and density of any liquid by putting the liquid into hollow space 4, and measure any of a change in resonance frequency, a change in resonant wavelength and an absolute value of the resonance frequency. This structure can eliminate a process of disposing acceptors 7 (77) on the surfaces of metal layers 2 and 3, hence improving the manufacturing efficiency of plasmon sensor 1.

A result of analysis on a sample case having acceptors 77 disposed on upper surface 3A of metal layer 3 will be described.

Figure 6:
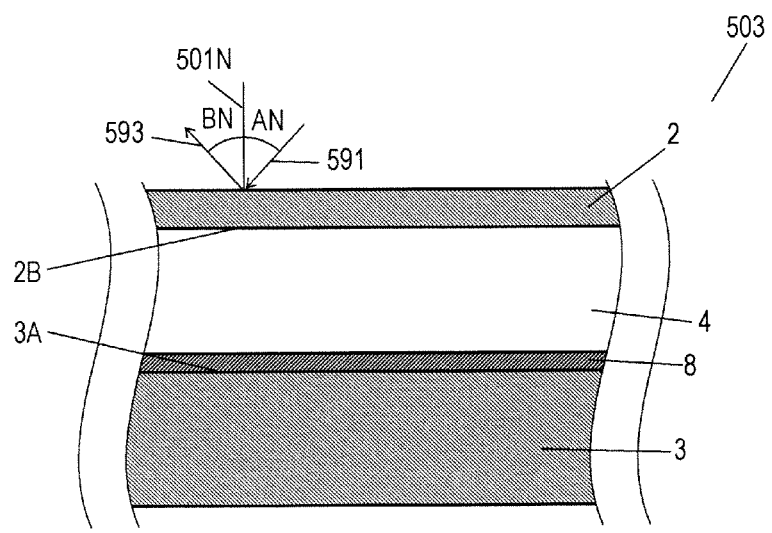
FIG. 6 is a schematic view of another analysis model of an electromagnetic field simulation of the plasmon sensor according to Embodiment 1.

FIG. 6 is a schematic view of another analysis model 503 of an electromagnetic field simulation of plasmon sensor 1. In FIG. 6, components identical to those of analysis models 501 and 502 shown in FIGS. 4A and 4B are denoted by the same reference numerals. In model 503, acceptors 7 are not provided on lower surface 2B of metal layer 2, but acceptors 77 are disposed on upper surface 3A of metal layer 3. Therefore, analyte 8 is provided not on lower surface 2B of metal layer 2, but on upper surface 3A of metal layer 3.

In analysis model 503 shown in FIG. 6, analyte 8 provided on upper surface 3A of metal layer 3 has a thickness of 10 nm and a relative dielectric constant of 3.0. A spatial thickness of hollow space 4 is 150 nm, and the space has a relative dielectric constant of 1.0.

The electromagnetic field simulation analysis was conducted on analysis model 503 by applying electromagnetic wave 591 at descending angle AN of 45 degrees with respect to the normal direction 501N perpendicular to upper surface 2A of metal layer 2, and detecting electromagnetic wave 593 radiated from upper surface 2A of metal layer 2 at an ascending angle of −45 degrees.

Figure 7:
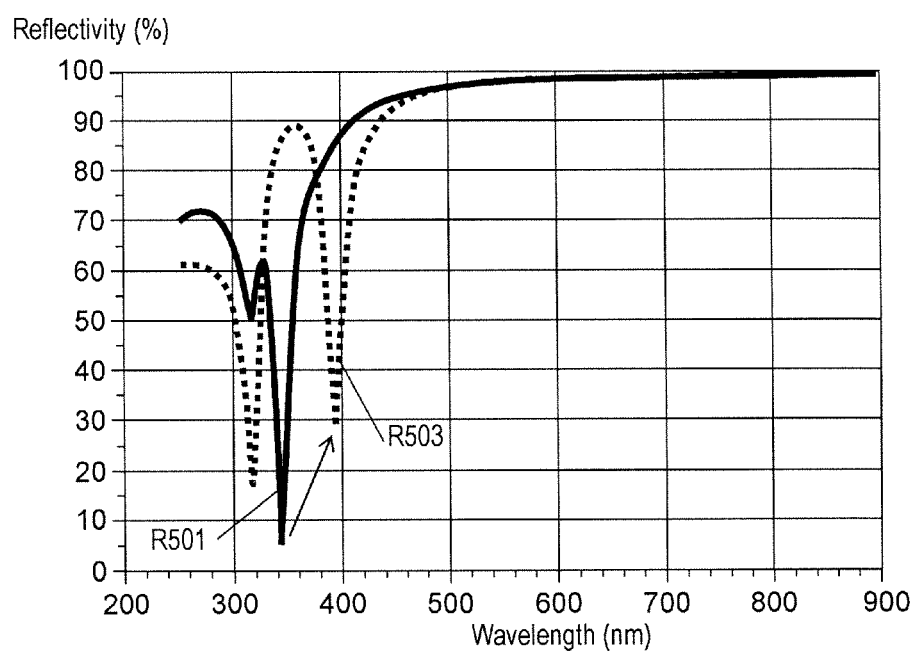
FIG. 7 shows an analysis result of the simulation of the plasmon sensor according to Embodiment 1.

FIG. 7 shows analysis results of the electromagnetic field simulation made on analysis models 501 and 503 shown in FIGS. 4A and 6. In FIG. 7, the horizontal axis represents the wavelength of electromagnetic wave 591, and the vertical axis represents reflectivity which is the ratio of power of electromagnetic wave 593 to power of electromagnetic wave 591. FIG. 7 shows respective reflectivities R501 and R503 of analysis models 501 and 503.

As shown in FIG. 7, a change in the resonant wavelength is observed even when analyte 8 is provided on upper surface 3A of metal layer 3. This indicates that surface plasmon resonance is generated on upper surface 3A of metal layer 3. In other words, it is adequate to provide acceptors 77 on upper surface 3A of metal layer 3 without having acceptors 7 on lower surface 2B of metal layer 2, and this can hence improve flexibility in designing plasmon sensor 1.

Plasmon sensor 1 may include acceptors 7 disposed on lower surface 2B of metal layer 2 and acceptors 77 disposed on upper surface 3A of metal layer 3. Plasmon sensor 1 having an advantage of use of the surface plasmon resonance occurring on both of lower surface 2B of metal layer 2 and upper surface 3A of metal layer 3, thereby providing plasmon sensor 1 with high sensitivity.

Figure 8A:
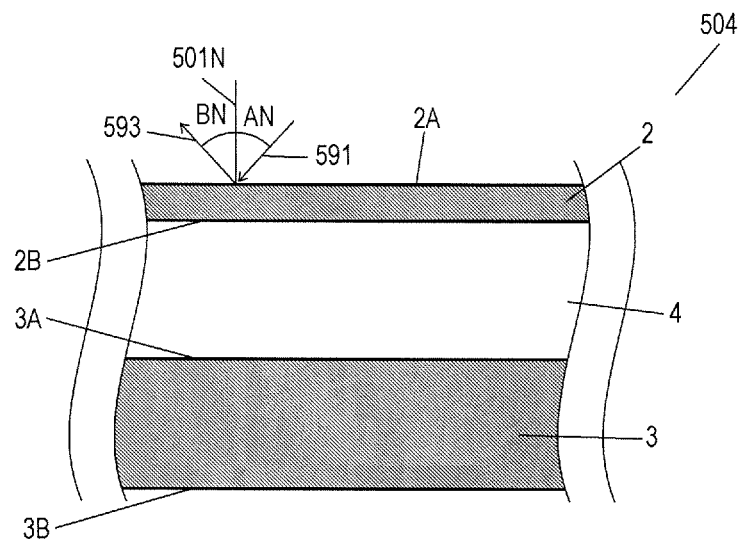
FIG. 8A is a schematic view of still another analysis model of an electromagnetic field simulation of the plasmon sensor according to Embodiment 1.
Figure 8B:
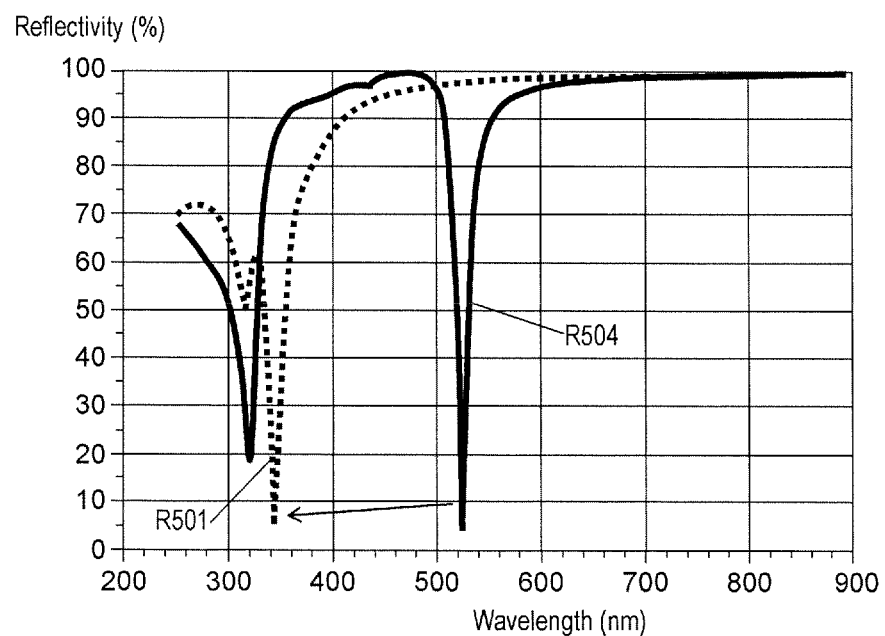
FIG. 8B shows an analysis result of the simulation of the plasmon sensor according to Embodiment 1.

FIG. 8A is a schematic view of analysis model 504 of an electromagnetic field simulation of plasmon sensor 1. In analysis model 504 of FIG. 8A, hollow space 4 has a relative dielectric constant of 2.0. FIG. 8B shows a result of the analysis made on analysis model 504. In FIG. 8B, the horizontal axis represents the wavelength of electromagnetic wave 591, and the vertical axis represents the reflectivity which is the ratio of power of electromagnetic wave 593 to power of electromagnetic wave 591. Analysis model 504 exhibits reflectivity R504.

As shown in FIGS. 5, 7 and 8B, surface plasmon resonance occurs even when hollow space 4 is in vacuum or filled with air, that is, even if hollow space 4 is not filled with a dielectric substance of a solid form having a high dielectric constant.

In plasmon sensor 1, hollow space 4 formed between metal layers 2 and 3 is not filled with a solid dielectric substance. This structure allows test sample 62 containing analyte 8 to be put into hollow space 4 and to allow analyte 8 to contact acceptors 7 (77).

The use of air or vacuum as medium 61 in hollow space 4 to reduce the relative dielectric constant can shorten the resonant wavelength of the surface plasmon resonance, as shown in FIG. 8B. In other words, plasmon sensor 1 having hollow space 4 filled with air or in vacuum allows a larger spatial distance between metal layers 2 and 3 for obtaining the same resonance frequency than a plasmon sensor having a hollow space filled with other dielectric substance.

Hollow space 4 is in vacuum or filled with air having the relative dielectric constant of about 1.0 or any other gas having a small relative dielectric constant similarly to plasmon sensor according to Embodiment 1. This structure allows the spatial distance between metal layers 2 and 3 to be longer than other plasmon sensors having a hollow space filled with a solid dielectric substance between metal layers 2 and 3. This structure can hence increase the thickness of hollow space 4, thereby allowing test sample 62 containing analyte 8 to be put easily into hollow space 4.

Figure 9A:
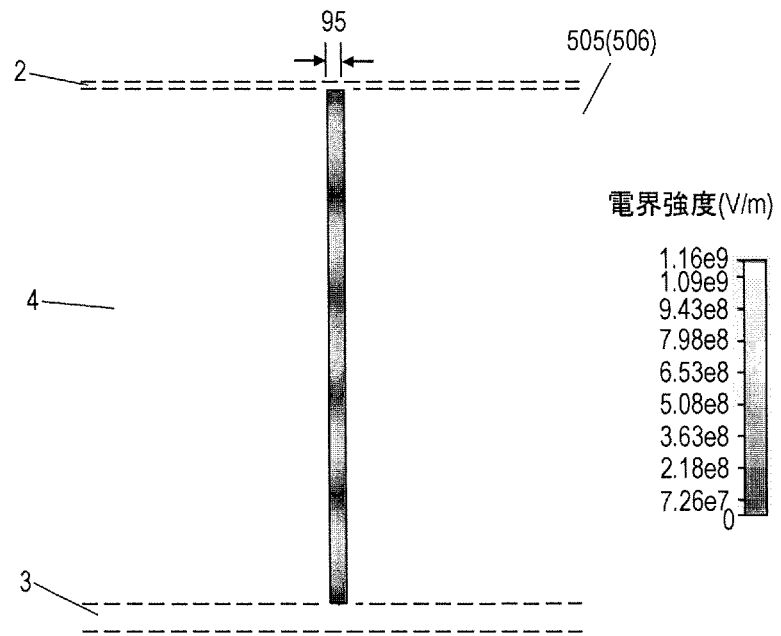
FIG. 9A shows an analysis result of the simulation of the plasmon sensor according to Embodiment 1.
Figure 9B:
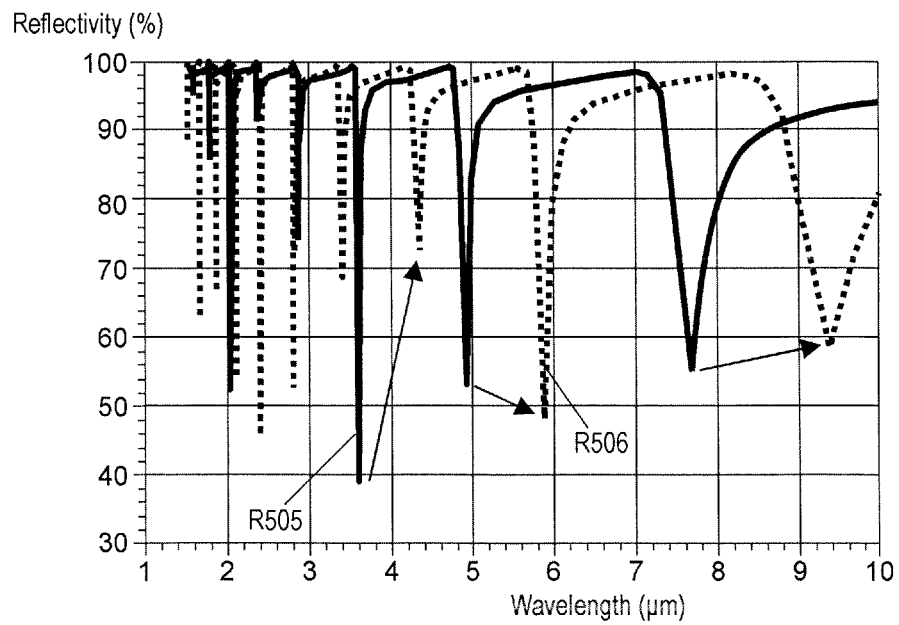
FIG. 9B shows an analysis result of the simulation of the plasmon sensor according to Embodiment 1.

In addition, the electromagnetic field intensity can be distributed in a high-order mode between metal layers 2 and 3 at the resonance frequency. That is, the electromagnetic field generated between metal layers 2 and 3 may have a high intensity locally at plural positions. FIGS. 9A and 9B show results of the electromagnetic field simulation performed on analysis model 505 of the same configuration as analysis model 501 shown in FIG. 4A except that the thickness of hollow space 4 is 10 µm.

The model shown in FIG. 9A has a resonant wavelength of 2883 nm. FIG. 9A shows distribution of the electric field intensity inside hollow space 4. In FIG. 9A, the distribution of the electric field of only partial region 95 is shown rather than the entire region of hollow space 4 to simplify the explanation.

In FIG. 9A, the electric field intensity in the space between metal layers 2 and 3 exhibits variations cyclically and locally along the direction from metal layer 2 toward metal layer 3, and the electric field intensity is low in the regions adjacent to metal layers 2 and 3. In FIG. 9A, the electric field has high intensity locally at plural positions, i.e., in five regions between metal layers 2 and 3, thus indicating the distribution of the electromagnetic field intensity in a high-order mode that is higher than the fundamental mode.

The electromagnetic field intensity distributed in the high-order mode between metal layers 2 and 3 provides an advantage of increasing the spatial distance between metal layers 2 and 3 to allow test sample 62 containing analyte 8 to be put easily into hollow space 4.

In analysis model 505 shown in FIG. 9A, hollow space 4 has a relative dielectric constant of 1.0. FIG. 9B shows reflectivities R505 and R506 representing results of the electromagnetic field simulation performed on analysis model 505 and analysis model 506 having the same configuration as analysis model 505 except for the hollow space having a relative dielectric constant of 1.2.

As shown in FIG. 9B, the surface plasmon resonance is generated in various resonant wavelengths in both of analysis models 505 and 506. It also shows that the resonant wavelength changes according to the change of a state of medium 61, the relative dielectric constant in hollow space 4.

If the thickness of hollow space 4 is increased, the electromagnetic field intensity distribution of a high-order mode occurs between metal layers 2 and 3, and surface plasmon resonance of a high-order frequency is generated, as discussed above.

Plasmon sensor 1 may also detect a temporal variation in the state of medium 61 inside hollow space 4 by using the surface plasmon resonance generated in frequencies of high-order mode. This provides the advantage of increasing the spatial distance between metal layers 2 and 3, accordingly allowing test sample 62 containing analyte 8 to be put easily into hollow space 4.

According to Embodiment 1, "adjacent region (first adjacent region) near lower surface 2B of metal layer 2" is either a region facing lower surface 2B of metal layer 2 or a region spaced from lower surface 2B of metal layer 2 by a predetermined distance (separated by, e.g. a resin spacer) while "adjacent region (second adjacent region) near upper surface 3A of metal layer 3" is either a region facing upper surface 3A of metal layer 3 or a region spaced from upper surface 3A of metal layer 3 by a predetermined distance (separated by, e.g. a resin spacer).

The term "acceptor" according to Embodiment 1 indicates a capturing body for making specific binding with a specific analyte, and indicates an antibody, receptor protein, aptamer, porphyrin, and high-polymer molecule produced by the molecular imprinting technique. The molecular imprinting technique is one of the concepts and techniques of template synthesis, and it indicates the technology aimed at constructing a complementary structure to a template molecule and a space in the high-polymer molecule. Since this space constructed in the high-polymer molecule is custom-made with respect to the shape of template molecule during the process of polymer synthesis, it can be anticipated to function as a part of selective binding. The high-polymer molecule produced by the molecular imprinting technique includes, for example, methacrylate group resin, styrene divinyl-benzene group resin, as well as molecular imprinted hydrogel and the like material composed by using acrylic acid or methacrylic acid (functional monomer), N-isopropyl acrylamide (structure-forming monomer), N,N'-methylene-bis-acrylamide (cross-linking agent).

When receptor protein is used as an acceptor, it becomes easy to select a suitable type of receptor protein for detection of the target material since a substantial database is available for the pairs of specific binding with receptor proteins.

The sensibility of the plasmon sensor can be improved if porphyrin is used as acceptors 7 and 77. This is because a peak wavelength of the absorption spectrum and absorbance of the porphyrin itself change when it is bound specifically with the target material.

In the case that aptamer is used as acceptors 7 and 77, an aptamer suitable for specific binding with the target material of detection can be designed, hence providing the desired plasmon sensor easily. In addition, the plasmon sensor can be stored for a long period of time since the aptamer can be stable for a long period of time.

A high-polymer molecule produced by the molecular imprinting technique, upon being used as acceptors 7 and 77, can improve the flexibility of designing the plasmon sensor since it is easy to design the high-polymer molecule suitable for making specific binding with the target material of detection. Furthermore, the use of high-polymer molecule can increase a selectable range of the plasmon resonant wavelength in designing the plasmon sensor since the high-polymer molecule capable of specific-binding with the target material of detection can have a smaller size than the aptamer.

In plasmon sensor 1 shown in FIG. 1, lower surface 5B of supporter 5 is designed to have a surface area larger than that of metal layer 2, but this is not necessarily restrictive. The area of metal layer 3 may be smaller than that of upper surface 6A of supporter 6, providing similar effects.

Figure 10A:
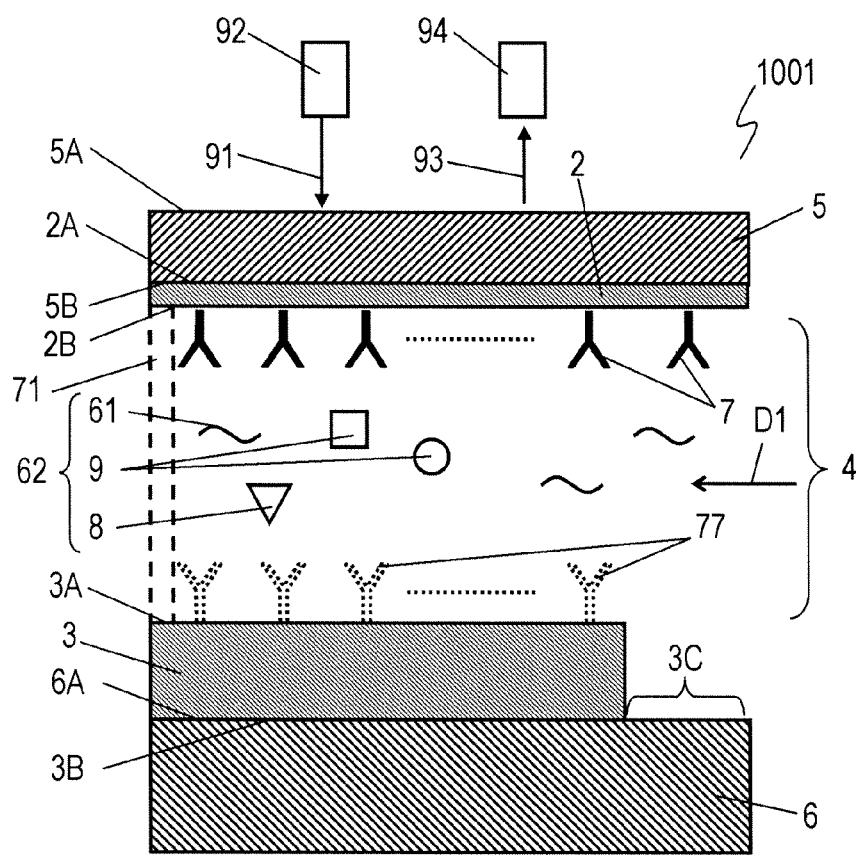
FIG. 10A is a cross-sectional view of another plasmon sensor according to Embodiment 1.

FIG. 10A is a cross-sectional view of another plasmon sensor 1001 according to Embodiment 1. In FIG. 10A, components identical to those of plasmon sensor 1 shown in FIG. 1 are denoted by the same reference numerals. In plasmon sensor 1001 shown in FIG. 10A, the area of lower surface 5B of supporter 5 is the same as that of metal layer 2, and lower surface 5B of supporter 5 does not contact or face hollow space 4. Instead, the area of metal layer 3 in plasmon sensor 1001 is smaller than that of upper surface 6A of supporter 6. In other words, upper surface 6A of supporter 6 has region 3C that faces and contacts hollow space 4. Region 3C has hydrophilic property similar to region 2C shown in FIG. 1, hence providing similar advantageous effects. In plasmon sensor 1001, however, supporter 5 may not necessarily have hydrophilic property.

Figure 10B:
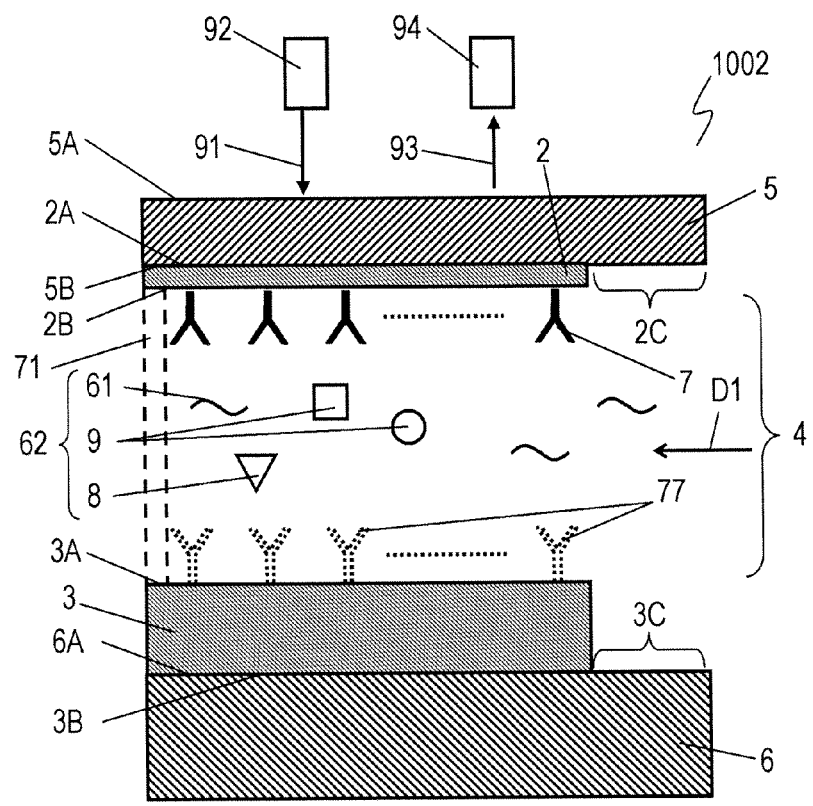
FIG. 10B is a cross-sectional view of still another plasmon sensor according to Embodiment 1.

FIG. 10B is a cross-sectional view of still another plasmon sensor 1002 according to Embodiment 1. In FIG. 10B, components identical to those of plasmon sensor 1001 shown in FIG. 10A are denoted by the same reference numerals. In plasmon sensor 1002 shown in FIG. 10B, the area of lower surface 5B of supporter 5 is larger than that of metal layer 2. Lower surface 5B of supporter 5 faces and contacts hollow space 4. In addition, the area of metal layer 3 is smaller than that of upper surface 6A of supporter 6 such that upper surface 6A of supporter 6 has region 3C that faces and contacts hollow space 4. Both supporters 5 and 6 have hydrophilic property. That is, region 3C has the hydrophilic property like region 2C shown in FIG. 1, hence providing similar advantageous effects.

In plasmon sensor 1 shown in FIG. 1, the area of lower surface 5B of supporter 5 is substantially equal to the area of upper surface 6A of supporter 6, but this is not necessarily restrictive. The area of lower surface 5B of supporter 5 may be different from the area of upper surface 6A of supporter 6. This structure can increase a boundary area between hollow space 4 and the other regions, allowing test sample 62 to be put into hollow space 4 easily.

Figure 11:
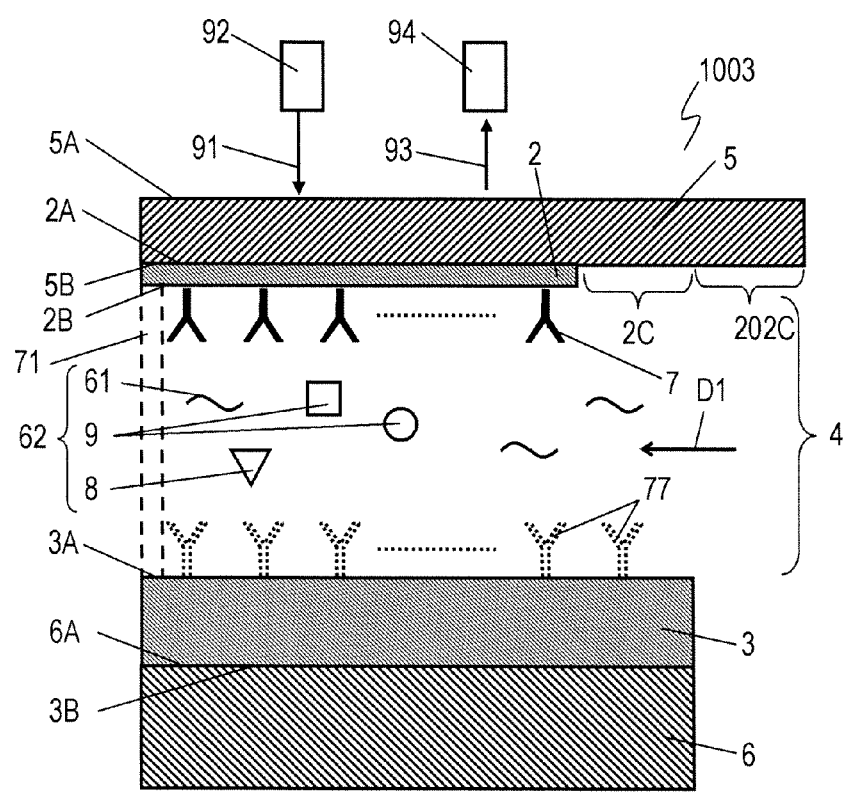
FIG. 11 is a cross-sectional view of a further plasmon sensor according to Embodiment 1.

FIG. 11 is a cross-sectional view of further plasmon sensor 1003 according to Embodiment 1. In FIG. 11, components identical to those of plasmon sensor 1 shown in FIG. 1 are denoted by the same reference numerals. In plasmon sensor 1003 shown in FIG. 11, the area of lower surface 5B of supporter 5 is larger than the area of upper surface 6A of supporter 6. That is, the area of lower surface 5B is different from that of upper surface 6A. More specifically, lower surface 5B of supporter 5 has region 202C connected to region 2C and extending to the edge of lower surface 5B. Region 202C has hydrophilic property like region 2C. Region 202C does not face metal layer 3. Test sample 62 contacts region 202C. This structure can increase the contacting area between plasmon sensor 1 and test sample 62, and allow test sample 62 to be put into hollow space 4 in the direction D1 more easily.

Supporters 5 and 6 having hydrophilic property are made of material having a functional group with a polarity on the surface thereof. The functional group includes OH$^-$. and NH2$^-$. The material having the functional group OH$^-$. on the surface includes glass (SiO$_2$).

As discussed above, one of supporters 5 and 6 has hydrophilic property. In the case that supporter 5 has hydrophilic property, the area of metal layer 2 is smaller than that of lower surface 5B of supporter 5. In the case that supporter 6 has hydrophilic property, the area of metal layer 3 is smaller than that of upper surface 6A of supporter 6. Another of supporters 5 and 6 may not necessarily have hydrophilic property.

In other words, lower surface 5B of supporter 5 has region 2C that faces hollow space 4 in the case that supporter 5 has the hydrophilic property. Upper surface 6A of supporter 6 has region 3C that faces hollow space 4 in the case that supporter 6 has the hydrophilic property.

In the case that supporter 5 has the hydrophilic property, region 2C of lower surface 5B of supporter 5 may be located at an edge of lower surface 5B of supporter 5. In the case that supporter 6 has hydrophilic property, region 3C of upper surface 6A of supporter 6 may be located at an edge of upper surface 6A of supporter 6.

Another of supporters 5 and 6 may have hydrophilic property.

Exemplary Embodiment 2

Figure 12:
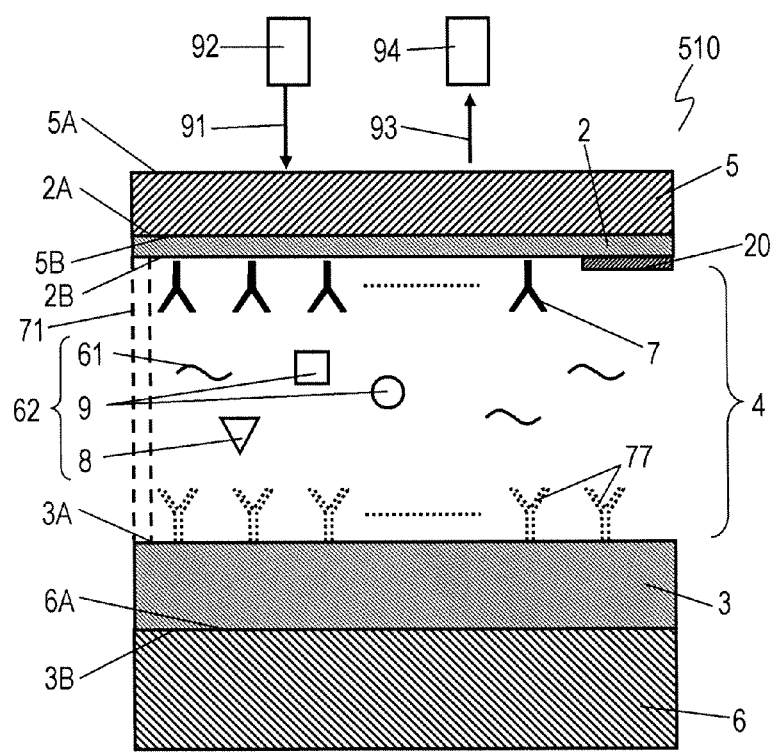
FIG. 12 is a cross-sectional view of a plasmon sensor according to Exemplary Embodiment 2 of the invention.

FIG. 12 is a cross-sectional view of plasmon sensor 510 according to Exemplary Embodiment 2 of the present invention. In FIG. 12, components identical to those of plasmon sensor 1 according to Embodiment 1 are denoted by the same reference numerals. Unlike plasmon sensor 1 of Embodiment 1, plasmon sensor 510 according to Embodiment 2 does not have region 2C that exposes supporter 5 having hydrophilicity. In other words, metal layer 2 has the same area as that of lower surface 5B of supporter 5. Instead of region 2C, hydrophilic material layer 20 is disposed on lower surface 2B of metal layer 2.

As shown in FIG. 12, plasmon sensor 510 according to Embodiment 2 includes metal layer 2 having lower surface 2V and upper surface 2A which is configured to receive electromagnetic wave, metal layer 3 having upper surface 3A facing lower surface 2B of metal layer 2, supporter 5 disposed on the upper surface of metal layer 2, supporter 6 disposed on the lower surface of metal layer 3, and spacer 71 that maintains a predetermined distance between metal layer 2 and metal layer 3. Hollow space 4 is provided between metal layers 2 and 3, and is configured to be filled with test sample 62 containing a medium.

In plasmon sensor 510 according to Embodiment 2, hydrophilic material layer 20 is disposed on lower surface 2B of metal layer 2. Hydrophilic material layer 20 is made of hydrophilic material. For example, hydrophilic material layer 20 is made of material that has a functional group having a polarity on a surface thereof. The functional group includes OH. and NH$_2$. The material having the functional group OH. on the surface includes glass (SiO$_2$). Hydrophilic material layer 20 facilitates introduction of test sample 62 into hollow space 4 by capillary phenomenon similarly to plasmon sensor 1 of Embodiment 1.

Plasmon sensor 510 illustrated in FIG. 12 includes hydrophilic material layer 20 disposed on lower surface 2B of metal layer 2, hydrophilic material layer 20 may be disposed on a part of at least one of the lower surface 2B of metal layer 2, the lower surface of supporter 5, the upper surface of metal layer 3 and the upper surface of supporter 6, thereby facilitating the introduction of test sample 62 into hollow space 4 by capillary phenomenon.

Figure 13A:
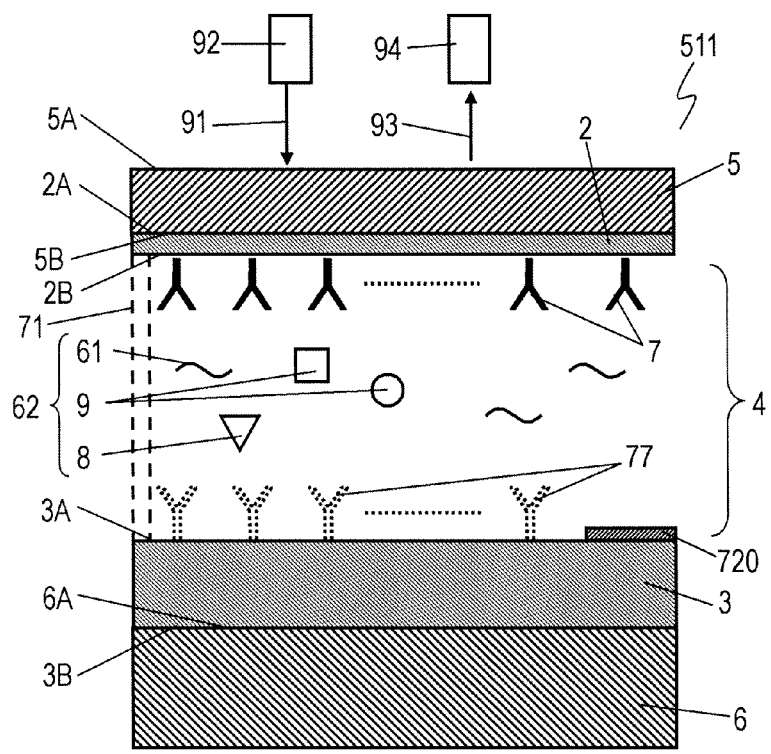
FIG. 13A is a cross-sectional view of another plasmon sensor according to Embodiment 2.

FIG. 13A is a cross-sectional view of another plasmon sensor 511 according to Embodiment 2. In FIG. 13A, components identical to those of plasmon sensor 510 shown in FIG. 12 are denoted by the same reference numerals. Plasmon sensor 511 shown in FIG. 13A includes hydrophilic material layer 720 made of hydrophilic material disposed on an edge portion of upper surface 3A of metal layer 3 instead of hydrophilic material layer 20 of plasmon sensor 510 shown in FIG. 12. Hydrophilic material layer 720 provides plasmon sensor 511 with advantageous effects similar to those of plasmon sensor 510 shown in FIG. 12.

Figure 13B:
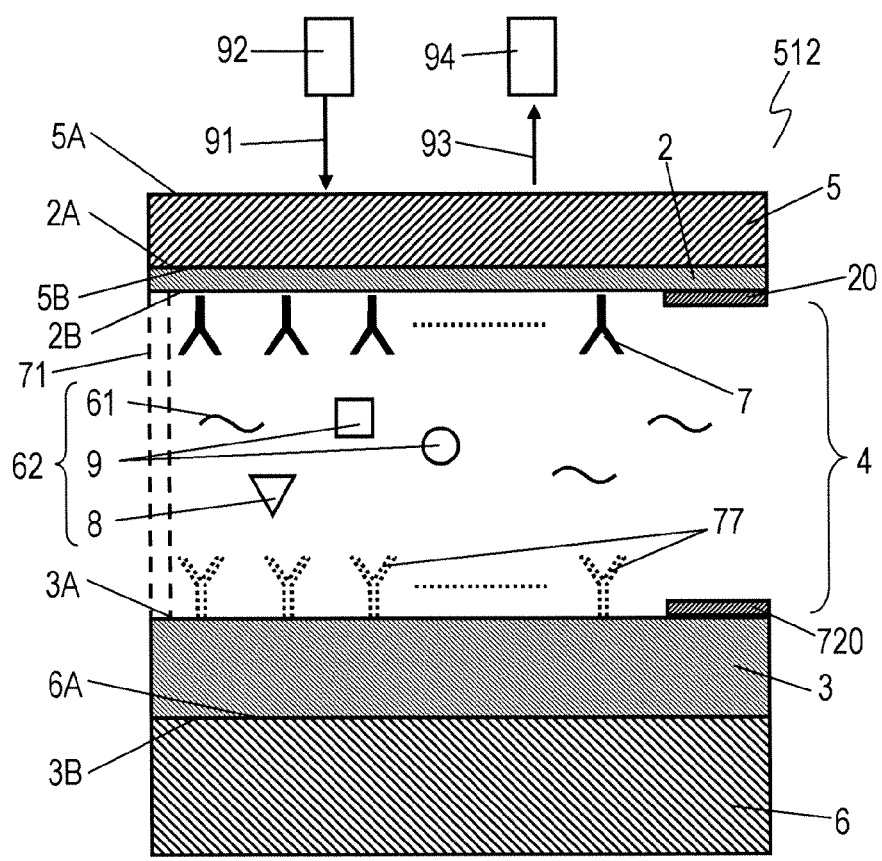
FIG. 13B is a cross-sectional view of still another plasmon sensor according to Embodiment 2.

FIG. 13B is a cross-sectional view of still another plasmon sensor 512 according to Embodiment 2. In FIG. 13B, components identical to those of plasmon sensor 510 shown in FIG. 12 are denoted by the same reference numerals. Plasmon sensor 512 shown in FIG. 13B further includes hydrophilic material layer 720 made of hydrophilic material disposed at an edge portion of upper surface 3A of metal layer 3 in addition to hydrophilic material layer 20 of plasmon sensor 510 shown in FIG. 12. Hydrophilic material layer 720 provides plasmon sensor 512 with advantageous effects similar to those of plasmon sensor 510 shown in FIG. 12.

Hydrophilic material layer 20 is not necessarily disposed directly on lower surface 2B of metal layer, as shown in FIG. 12. Hydrophilic material layer 20 may be disposed at a lower region spaced from lower surface 2B of metal layer 2 by a predetermined distance. For example, hydrophilic material layer 20 may be placed via an adhesive layer that fixes hydrophilic material layer 20. Test sample 62 can be introduced easily into hollow space 4 by the capillary phenomenon if hydrophilic material layer 20 is placed at a part of the region facing hollow space 4. Hydrophilic material layer 20 may be is placed at any of a region below supporter 5, a region above metal layer 3, and a region above supporter 6, providing similar advantageous effects.

Hydrophilic material layer 720 is not necessarily disposed directly on upper surface 3A of metal layer 3, as shown in FIGS. 13A and 13B. Hydrophilic material layer 720 may be disposed to an upper position spaced from upper surface 3A of metal layer 3 by a predetermined distance. For example, hydrophilic material layer 720 may be placed via an adhesive layer that fixes hydrophilic material layer 720 to upper surface 3A of metal layer 3. Test sample 62 can be introduced easily into hollow space 4 by the capillary phenomenon if hydrophilic material layer 720 is placed at a part of the region facing hollow space 4. Hydrophilic material layer 720 may be placed at any of a region below supporter 5, a region above metal layer 3, and a region above supporter 6, providing similar advantageous effects.

Hydrophilic material layer 20 existing at a part or entire of a region along the edge of lower surface 2B of metal layer 2 contacts test sample 62 easily, hence facilitating the introducing of the test sample by the capillary phenomenon. Even if hydrophilic material layer 20 does not exist at a part or entire of the region along the edge of lower surface 2B of metal layer 2, test sample 62 can be introduced by the capillary phenomenon more easily than a structure not including hydrophilic material layer 20. Hydrophilic material layer 20 may be placed at any of a region above metal layer 3, a region below supporter 5, and a region above supporter 6, providing similar advantageous effects.

Hydrophilic material layer 720 existing at a part or entire of a region along the edge of upper surface 3A of metal layer 3 facilitates the introducing of the test sample by the capillary phenomenon since test sample 62 contacts hydrophilic material layer 720 easily. Even if hydrophilic material layer 720 does not exist at the part or entire of the region along the edge of upper surface 3A of metal layer 3, test sample 62 can be introduced by the capillary phenomenon more easily than a structure not having hydrophilic material layer 720. Hydrophilic material layer 20 can be placed at any of a region below metal layer 2, a region below supporter 5, and a region above supporter 6, providing similar advantageous effects.

In Embodiments 1 and 2, terms, such as 1 "upper surface", "lower surface", "above" and "below", indicating directions indicate relative directions dependent only upon relative positions of components of the plasmon sensors, and do not indicate absolute directions, such as a vertical direction.

INDUSTRIAL APPLICABILITY

A plasmon sensor according to the present invention has a small size and a simple structure, and it is therefore useful for, e.g. a small, low-cost biosensor.

REFERENCE MARKS IN THE DRAWINGS

1 Plasmon Sensor
2 Metal Layer (First Metal Layer)
2C Region (First Region)
3 Metal Layer (Second Metal Layer)
3C Region (Second Region)
4 Hollow Space
5 Supporter (First Supporter)
6 Supporter (Second Supporter)
7 Acceptor
8 Analyte
20 Hydrophilic Material Layer

The invention claimed is:

1. A plasmon sensor comprising:
a first supporter transparent to an electromagnetic wave;
a second supporter;
a first metal layer disposed on the first supporter, the first metal layer allowing the electromagnetic wave to pass through the first metal layer; and
a second metal layer confronting the first metal layer and disposed on the second supporter, wherein:
a hollow space is provided between the first supporter and the second supporter,
the first supporter has a first region exposed to the hollow space,
the first region is located at an end of the hollow space,
the first region is hydrophilic, and the first metal layer and the second metal layer are hydrophobic, and
a thickness of the first metal layer is smaller than a thickness of the second metal layer.

2. The plasmon sensor according to claim 1, wherein:
the second supporter has a second region exposed to the hollow space,
the second region is located at an end of the hollow space, and
the second region is hydrophilic.

3. The plasmon sensor according to claim 1, further comprising a plurality of acceptors disposed on a surface of at least one of the first metal layer and the second metal layer.

4. The plasmon sensor according to claim 1, wherein an area of the second metal layer is smaller than an area of the second supporter.

5. The plasmon sensor according to claim 1, wherein a thickness of the first supporter is smaller than a thickness of the second supporter.

6. The plasmon sensor according to claim 1, wherein the first supporter comprises glass.

7. The plasmon sensor according to claim 1, wherein the electromagnetic wave is a visible light.

8. The plasmon sensor according to claim 1, wherein the hollow space extends from a first end of the first supporter to a second end of the first supporter.

9. A plasmon sensor comprising:
a first supporter transparent to an electromagnetic wave;
a second supporter;
a first metal layer disposed on the first supporter, the first metal layer allowing the electromagnetic wave to pass through the first metal layer;
a second metal layer confronting the first metal layer and disposed on the second supporter; and
a first hydrophilic region disposed on the first metal layer or the first supporter, wherein:
a hollow space is provided between the first supporter and the second supporter,
the first hydrophilic region is provided at an end of the hollow space,
the first hydrophilic region is exposed to the hollow space,
the first hydrophilic region is hydrophilic, and the first metal layer and the second metal layer are hydrophobic, and
a thickness of the first metal layer is smaller than a thickness of the second metal layer.

10. The plasmon sensor according to claim 9, further comprising a plurality of acceptors disposed on a surface of at least one of the first metal layer and the second metal layer.

11. The plasmon sensor according to claim 9, wherein a thickness of the first supporter is smaller than a thickness of the second supporter.

12. The plasmon sensor according to claim 9, wherein an area of the second metal layer is smaller than an area of the second supporter.

13. The plasmon sensor according to claim 9, wherein the first hydrophilic region is made of a hydrophilic material which is disposed on the first metal layer or the first supporter.

14. The plasmon sensor according to claim 9, wherein the electromagnetic wave is a visible light.

15. The plasmon sensor according to claim 9, wherein the hollow space extends from a first end of the first supporter to a second end of the first supporter.

16. The plasmon sensor according to claim 9, further comprising:
a second hydrophilic region disposed on the second metal layer or the second supporter, wherein:
the second hydrophilic region is provided at an end of the hollow space,
the second hydrophilic region is exposed to the hollow space, and
the second hydrophilic region is hydrophilic.

17. The plasmon sensor according to claim 16, wherein the second hydrophilic region is made of a hydrophilic material which is disposed on the second metal layer or the second supporter.

18. A plasmon sensor comprising:
a first supporter transparent to an electromagnetic wave;
a second supporter;
a first metal layer disposed on the first supporter, the first metal layer allowing the electromagnetic wave to pass through the first metal layer; and
a second metal layer confronting the first metal layer and disposed on the second supporter, wherein:
a hollow space is provided between the first supporter and the second supporter,
an end of the first supporter protrudes from an end of the hollow space so as to form a protruding portion,
the protruding portion is hydrophilic, and the first metal layer and the second metal layer are hydrophobic, and
a thickness of the first metal layer is smaller than a thickness of the second metal.

19. The plasmon sensor according to claim 18, further comprising a plurality of acceptors disposed on a surface of at least one of the first metal layer and the second metal layer.

20. The plasmon sensor according to claim 18, wherein a thickness of the first supporter is smaller than a thickness of the second supporter.

21. The plasmon sensor according to claim 18, wherein an area of the second metal layer is smaller than an area of the second supporter.

22. The plasmon sensor according to claim 18, further comprising:
a first hydrophilic material layer made of a hydrophilic material disposed on a surface of the protruding portion.

23. The plasmon sensor according to claim 18, wherein the first supporter comprises glass.

24. The plasmon sensor according to claim 18, wherein the electromagnetic wave is a visible light.

25. A plasmon sensor comprising:
a first supporter transparent to an electromagnetic wave;
a second supporter;
a first metal layer disposed on the first supporter, the first metal layer allowing the electromagnetic wave to pass through the first metal layer; and
a second metal layer confronting the first metal layer and disposed on the second supporter, wherein:
a hollow space is provided between the first supporter and the second supporter,
the first supporter has a first region exposed to the hollow space,
the first region is located at an end of the hollow space,
the first region is hydrophilic, and the first metal layer and the second metal layer are hydrophobic, and
a thickness of the first supporter is smaller than a thickness of the second supporter.

26. A plasmon sensor comprising:
a first supporter transparent to an electromagnetic wave;
a second supporter;
a first metal layer disposed on the first supporter, the first metal layer allowing the electromagnetic wave to pass through the first metal layer;
a second metal layer confronting the first metal layer and disposed on the second supporter; and
a first hydrophilic region disposed on the first metal layer or the first supporter, wherein:
a hollow space is provided between the first supporter and the second supporter,
the first hydrophilic region is provided at an end of the hollow space,
the first hydrophilic region is exposed to the hollow space,
the first hydrophilic region is hydrophilic, and the first metal layer and the second metal layer are hydrophobic, and
a thickness of the first supporter is smaller than a thickness of the second supporter.

27. A plasmon sensor comprising:
a first supporter transparent to an electromagnetic wave;
a second supporter;
a first metal layer disposed on the first supporter, the first metal layer allowing the electromagnetic wave to pass through the first metal layer; and
a second metal layer confronting the first metal layer and disposed on the second supporter, wherein:
a hollow space is provided between the first supporter and the second supporter,
an end of the first supporter protrudes from an end of the hollow space so as to form a protruding portion,
the protruding portion is hydrophilic, and the first metal layer and the second metal layer are hydrophobic, and
a thickness of the first supporter is smaller than a thickness of the second supporter.

* * * * *